US008802588B2

(12) United States Patent
Zhou et al.

(10) Patent No.: US 8,802,588 B2
(45) Date of Patent: Aug. 12, 2014

(54) BISMUTH CATALYST COMPOSITION AND PROCESS FOR MANUFACTURING ETHANOL MIXTURE

(75) Inventors: Zhenhua Zhou, Houston, TX (US); Victor J. Johnston, Houston, TX (US); Heiko Weiner, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 258 days.

(21) Appl. No.: 13/356,189

(22) Filed: Jan. 23, 2012

(65) Prior Publication Data

US 2013/0190527 A1   Jul. 25, 2013

(51) Int. Cl.
*B01J 23/00* (2006.01)
*B01J 23/50* (2006.01)
*C07C 27/04* (2006.01)
*C07C 37/02* (2006.01)
*C07C 67/48* (2006.01)
*C07C 69/74* (2006.01)

(52) U.S. Cl.
USPC ............... 502/300; 502/325; 502/353; 560/1; 560/248; 560/265; 568/885

(58) Field of Classification Search
CPC .......... B01J 21/04; B01J 21/06; B01J 21/063; B01J 21/066; B01J 21/08; B01J 21/18; B01J 23/18; B01J 23/38; B01J 23/02; B01J 23/04; B01J 23/78; B01J 23/89; C07C 69/74; C07C 67/48; C07C 67/02; C07C 27/04
USPC ............... 502/300, 325, 353; 568/885; 560/1, 560/248, 265
See application file for complete search history.

(56) References Cited

U.S. PATENT DOCUMENTS

| 1,819,818 | A | * | 8/1931 | Jaeger ......................... 560/103 |
| 2,259,423 | A | * | 10/1941 | Kirkpatrick .................. 502/339 |
| 2,607,807 | A | | 8/1952 | Ford |
| 2,744,939 | A | | 5/1956 | Kennel |
| 3,478,112 | A | | 11/1969 | Karl et al. |
| 3,990,952 | A | | 11/1976 | Katzen et al. |
| 4,317,918 | A | | 3/1982 | Takano et al. |
| 4,395,576 | A | | 7/1983 | Kwantes et al. |
| 4,398,039 | A | | 8/1983 | Pesa et al. |
| 4,399,305 | A | | 8/1983 | Schreck |
| 4,407,733 | A | * | 10/1983 | Birkenstock et al. ......... 502/174 |
| 4,421,939 | A | | 12/1983 | Kiff et al. |
| 4,443,639 | A | | 4/1984 | Pesa et al. |
| 4,480,115 | A | | 10/1984 | McGinnis |
| 4,517,391 | A | | 5/1985 | Schuster et al. |
| 4,550,185 | A | | 10/1985 | Mabry et al. |
| 4,678,543 | A | | 7/1987 | Houben et al. |
| 4,692,218 | A | | 9/1987 | Houben et al. |
| 4,777,303 | A | | 10/1988 | Kitson et al. |
| 4,804,791 | A | | 2/1989 | Kitson et al. |
| 4,826,795 | A | | 5/1989 | Kitson et al. |
| 4,985,572 | A | | 1/1991 | Kitson et al. |
| 4,990,655 | A | | 2/1991 | Kitson et al. |
| 5,061,671 | A | | 10/1991 | Kitson et al. |
| 5,124,004 | A | | 6/1992 | Grethlein et al. |
| 5,137,861 | A | | 8/1992 | Shih et al. |
| 5,144,068 | A | | 9/1992 | Smith et al. |
| 5,149,680 | A | | 9/1992 | Kitson et al. |
| 5,155,084 | A | | 10/1992 | Horn et al. |
| 5,243,095 | A | | 9/1993 | Roberts et al. |
| 5,350,504 | A | | 9/1994 | Dessau |
| 5,821,111 | A | | 10/1998 | Grady et al. |
| 5,945,570 | A | | 8/1999 | Arhancet et al. |
| 6,049,008 | A | | 4/2000 | Roberts et al. |
| 6,204,417 | B1 | | 3/2001 | Fischer et al. |
| 6,232,352 | B1 | | 5/2001 | Vidalin et al. |
| 6,294,703 | B1 | | 9/2001 | Hara et al. |
| 6,462,231 | B1 | | 10/2002 | Yanagawa et al. |
| 6,495,730 | B1 | | 12/2002 | Konishi et al. |
| 6,509,180 | B1 | | 1/2003 | Verser et al. |
| 6,632,330 | B1 | | 10/2003 | Colley et al. |
| 6,657,078 | B2 | | 12/2003 | Scates et al. |
| 6,685,754 | B2 | | 2/2004 | Kindig et al. |
| 6,693,213 | B1 | | 2/2004 | Kolena et al. |
| 6,906,228 | B2 | | 6/2005 | Fischer et al. |
| 6,927,048 | B2 | | 8/2005 | Verser et al. |
| 7,297,236 | B1 | | 11/2007 | Vander Griend et al. |
| 7,425,657 | B1 | | 9/2008 | Elliott et al. |
| 7,507,562 | B2 | | 3/2009 | Verser et al. |

(Continued)

FOREIGN PATENT DOCUMENTS

| EP | 0175558 | 3/1986 |
| EP | 0990638 | 4/2000 |
| EP | 1262234 | 12/2002 |
| EP | 1277826 | 1/2003 |
| EP | 2186787 | 5/2010 |
| GB | 1168785 | 10/1969 |
| GB | 1559540 | 1/1980 |
| JP | 6-116182 | 4/1994 |
| JP | 10-306047 | 11/1998 |
| JP | 11-147845 | 6/1999 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379.

(Continued)

*Primary Examiner* — Patricia L Hailey

(57) ABSTRACT

The present invention relates to a catalyst composition comprising at least one Group VIII metal and bismuth on a support, and to a process for manufacturing a product comprising ethanol and ethyl acetate from a feedstock comprising acetic acid over the catalyst composition under hydrogenation conditions, including a temperature of greater than about 290° C.

20 Claims, No Drawings

(56) References Cited

U.S. PATENT DOCUMENTS

| | | |
|---|---|---|
| 7,538,060 B2 | 5/2009 | Barnicki et al. |
| 7,553,397 B1 | 6/2009 | Colley et al. |
| 7,572,353 B1 | 8/2009 | Vander Griend |
| 7,608,744 B1 | 10/2009 | Johnston et al. |
| 7,863,489 B2 | 1/2011 | Johnston et al. |
| 7,884,253 B2 | 2/2011 | Stites et al. |
| 2003/0077771 A1 | 4/2003 | Verser et al. |
| 2003/0104587 A1 | 6/2003 | Verser et al. |
| 2004/0009614 A1 | 1/2004 | Ahn et al. |
| 2004/0195084 A1 | 10/2004 | Hetherington et al. |
| 2006/0019360 A1 | 1/2006 | Verser et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2009/0023192 A1 | 1/2009 | Verser et al. |
| 2009/0166172 A1 | 7/2009 | Casey et al. |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0121114 A1 | 5/2010 | Johnston et al. |
| 2012/0010446 A1* | 1/2012 | Warner et al. ............ 568/885 |
| 2012/0157721 A1* | 6/2012 | Weiner et al. ............ 568/885 |
| 2013/0261347 A1* | 10/2013 | Scates et al. ............ 568/879 |
| 2013/0261348 A1* | 10/2013 | Scates et al. ............ 568/881 |
| 2013/0261349 A1* | 10/2013 | Weiner et al. ............ 568/885 |

FOREIGN PATENT DOCUMENTS

| | | |
|---|---|---|
| JP | 2001-046874 | 2/2001 |
| JP | 2001-157841 | 6/2001 |
| WO | WO 83/03409 | 10/1983 |
| WO | WO 2005/102513 | 11/2005 |
| WO | WO 2009/063176 | 5/2009 |
| WO | WO 2009/086839 | 7/2009 |
| WO | WO 2009/105860 | 9/2009 |
| WO | WO 2010/055285 | 5/2010 |

OTHER PUBLICATIONS

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Nefedov and I V Mishin B K, "Synthesis of diethyl ether in presence of zeolite catalysts", Russian Chem. Bull., Springer Anew York LLC, v. 28, Jan. 1, 1979, pp. 183-186.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

International Search Report and Written Opinion for PCT/US2009/004197 mailed Mar. 24, 2010.

International Search Report and Written Opinion for PCT/US2009/004195 mailed Mar. 26, 2010.

Written Opinion for PCT/US2010/054132 mailed Nov. 29, 2011.

Extended European Search Report mailed on Feb. 1, 2012 in corresponding European Application No. 11179239.6-2103.

\* cited by examiner

BISMUTH CATALYST COMPOSITION AND PROCESS FOR MANUFACTURING ETHANOL MIXTURE

FIELD OF THE INVENTION

The present invention relates to a catalyst composition comprising at least one Group VIII metal and bismuth on a support and to a process for manufacturing products comprising an ethanol mixture from a feedstock comprising acetic acid over the catalyst composition under hydrogenation conditions, including a temperature of greater than about 290° C.

BACKGROUND OF THE INVENTION

Ethanol and ethyl acetate for industrial use are conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP 0175558 and U.S. Pat. No. 4,398,039. A summary of some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon support. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

SUMMARY OF THE INVENTION

This invention is directed to a catalyst composition comprising at least one Group VIII metal and bismuth, on a support, e.g. silica, alumina, titania, silica/alumina, calcium metasilicate, pyrogenic silica, high purity silica, zirconia, carbon, zeolite and mixtures thereof, and to a process for manufacturing product comprising ethanol and ethyl acetate from feedstock comprising acetic acid and hydrogen over the catalyst composition under hydrogenation conditions including a temperature of greater than about 290° C.

One embodiment of the invention is a catalyst composition comprising from 0.25 wt. % to 2 wt. % active metals on a support selected from the group consisting of silica, alumina, titania, silica/alumina, calcium metasilicate, pyrogenic silica, high purity silica, zirconia, carbon, zeolite and mixtures thereof, said active metals comprising at least one Group VIII metal and bismuth, said catalyst composition comprising an excess molar amount of the at least one Group VIII metal. In another embodiment of the invention, the support further comprises a modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In one embodiment the support comprises silica and the support modifier is calcium metasilicate.

Another embodiment of the invention is a process for producing a product comprising ethanol and ethyl acetate which comprises contacting a feedstock comprising acetic acid and hydrogen in a reaction zone at hydrogenation conditions including a temperature of greater than about 290° C. with a catalyst composition, wherein the catalyst composition comprises from 0.25 wt. % to 2 wt. % active metals, and wherein the catalyst composition comprises an excess molar amount of the at least one Group VIII metal. In an embodiment of the invention, the hydrogenation conditions include a temperature from about 290° C. to 350° C, a pressure of 10 kPa to 3000 kPa, and hydrogen to acetic acid mole ratio of greater than 4:1.

DETAILED DESCRIPTION OF THE INVENTION

Catalyst Composition

The present invention relates to a catalyst composition having a support material on which certain active metals are impregnated, the catalyst composition comprising a specific amount of active metals comprising at least one Group VIII metal and bismuth. The Group VIII is selected from the group consisting of iron, cobalt, nickel, ruthenium, rhodium, platinum, palladium, and combinations thereof. Preferably, the Group VIII is selected from the group consisting of platinum, palladium and nickel. In one embodiment, the at least one Group VIII metal is in molar excess compared to bismuth.

Support Materials

The catalyst composition of the present invention may comprise any suitable support material. In one embodiment, the support material may be an inorganic oxide. In one embodiment, the support material may be selected from the group consisting of silica, alumina, titania, silica/alumina, calcium metasilicate, pyrogenic silica, high purity silica, zirconia, carbon, zeolite and mixtures thereof. In one preferred embodiment, the support material is selected from the group consisting of silica, alumina, silica/alumina, calcium metasilicate, and mixtures thereof. Preferably, the support material comprises silica. In preferred embodiments, the support material is present in an amount from 25 wt. % to 99 wt. %, e.g., from 30 wt. % to 98 wt. % or from 35 wt. % to 95 wt. %.

The surface area of siliceous support material, i.e., comprising silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the siliceous support material preferably has a surface area of from 50 to 600 $m^2/g$, e.g., from 100 to 500 $m^2/g$ or from 100 to 300 $m^2/g$. High surface area silica, as exemplified throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The siliceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the siliceous support material has a morphology that allows for a packing density of from 0.1 to 1.0 $g/cm^3$, e.g., from 0.2 to 0.9 $g/cm^3$ or from 0.3 to 0.8 $g/cm^3$. In terms of size, the siliceous support material preferably has an average particle size, e.g., meaning the diameter for spherical particles or equivalent spherical diameter for non-spherical particles, of from 0.01 to 1.0 cm, e.g., from 0.1 to 0.7 cm or from 0.2 to 0.5 cm. Since the one or more active metal(s) that are disposed on or within the support are generally very small in size, those active metals should not substantially impact the size of the overall catalyst particles. Thus, the above particle sizes generally apply to both the size of the support as well as the final catalyst particles.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$.

A preferred silica/alumina support material is KA-160 (Süd Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

Support Modifiers

The support material may also comprise a support modifier. In one embodiment, support modifiers are present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

A support modifier may adjust the acidity of the support material. For example, the acid sites, e.g. Bronsted acid sites, on the support material may be adjusted by the support modifier to favor selectivity to ethanol during the hydrogenation of acetic acid. The acidity of the support material may be adjusted by reducing the number or reducing the availability of Bronsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of a modified support that adjusts the acidity of the support to make the support less acidic or more basic favors formation of ethanol over other hydrogenation products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be crystalline or amorphous.

In some embodiments, there may be a basic modifier and an acidic modifier. $WO_3$ and $CaSiO_3$ may both be used on a silica or silica-alumina support material.

In one preferred embodiment, the support comprises silica that contains $CaSiO_3$ as a support modifier.

Active Metals

Active metals comprising at least one Group VIII metal and bismuth will be impregnated on the support such that the catalyst composition will comprise an excess molar amount of the at least one Group VIII metal. The total weight of all the active metals present in the catalyst preferably is from 0.25 wt. % to 1.5 wt. %, e.g., from 0.5 wt. % to 1.3 wt. %, or from 0.7 wt. % to 1.25 wt. %. In one embodiment, the metal loading of the bismuth may be from 0.1 to 1.5 wt. %, e.g., 0.2 to 1.25 wt. % or from 0.3 to 1 wt. %. For purposes of the present specification, unless otherwise indicated, weight percent is based on the total weight of the catalyst including metal and support.

The Group VIII metal may be selected from the group consisting of iron, cobalt, nickel, ruthenium, rhodium, platinum, palladium, osmium, iridium and combinations thereof. For purposes of the present invention, bismuth must also be present. Without being bound by theory the presence of bismuth may be a promoter for the Group VIII metal and improve conversion and selectivity. In one embodiment, the catalyst of the present invention may be substantially free of tin and/or zinc. Additional active metals may also be used in some embodiments. Therefore, non-limiting examples of active metals on the present catalyst composition, with an excess molar amount of the at least one Group VIII metal, include platinum/bismuth, palladium/bismuth, nickel/bismuth, platinum/nickel/bismuth, iron/platinum/bismuth, etc. The active metals may be alloyed with one another or may comprise a non-alloyed metal solutions or mixtures.

The molar ratio of Group VIII metal to bismuth is preferably greater than 1.1:1, e.g., greater than 1.5:1 or greater than 2:1 . An excess molar ratio of Group VIII metals to bismuth is preferred for producing ethanol mixtures.

In one preferred embodiment, the catalyst composition comprises 0.7 wt. % to 1.25 wt. % platinum and bismuth on a silica support. The silica support may also comprise a support modifier such as $CaSiO_3$.

Process for Making Catalyst

In one embodiment of making the catalyst composition, one or more support modifiers, if desired, may be added to the support by mixing or through impregnation. Powdered materials of the modified support or a precursor thereto may be pelletized, crushed and sieved. Drying may also be preformed after the support modifier is added.

The modified or unmodified support chosen for the catalyst composition may be shaped into particles having the desired size distribution, e.g., to form particles having an average particle size in the range of from 0.2 to 0.4 cm. The support may be extruded, pelletized, tabletized, pressed, crushed or sieved to the desired size distribution. Any of the known methods to shape the support material into desired size distribution can be employed.

In a preferred method of preparing the catalyst, the active metals are impregnated onto the modified or unmodified support. A precursor of the active metal preferably is used in the metal impregnation step, such as a water soluble compound or water dispersible compound/complex that includes the metal of interest. Depending on the metal precursor employed, the use of a solvent, such as water, glacial acetic acid or an organic solvent may be preferred. The next active metal precursor also preferably is impregnated into the support from a next metal precursor. If desired, a third metal or third metal precursor may also be impregnated into the support.

Impregnation occurs by adding, optionally drop wise, either or both the metal precursor and/or the next metal precursor and/or additional metal precursors, preferably in suspension or solution, to the dry support. The resulting mixture may then be heated, optionally under vacuum, in order to remove the solvent. Additional drying and calcining may then be performed, optionally with ramped heating, to form the final catalyst composition. Upon heating and/or the application of vacuum, the metals of the metal precursors preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the active metals (and optional additional metals) into the support may occur simultaneously (co-impregnation) or sequentially. In simultaneous impregnation, the metal precursors (and optionally additional metal precursors) are mixed together and added to the support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the active metal precursors in the event the two precursors are incompatible with the desired solvent, e.g., water.

In sequential impregnation, the first metal precursor is first added to the support followed by drying and calcining, and the resulting material is then impregnated with the next metal precursor followed by an additional drying and calcining step to form the final catalyst composition. Additional metal precursors (e.g., a third metal precursor) may be added either with the first and/or next metal precursor or a separate third impregnation step, followed by drying and calcination. Combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Non-limiting examples of suitable compounds for bismuth precursors include $Bi(NO_3)_3 \cdot 5H_2O$. Generally, both from the point of view of economics and environmental aspects, aqueous solutions of soluble compounds of platinum are preferred. A particularly preferred precursor to platinum is platinum ammonium nitrate, $Pt(NH_3)_4(NO_4)_2$. Calcining of the solution with the support and active metal may occur, for example, at a temperature of from 250° C. to 800° C., e.g., from 300° C. to 700° C. or about 500° C., optionally for a period of from 1 to 12 hours, e.g., from 2 to 10 hours, from 4 to 8 hours or about 6 hours.

As an example, $PtBi/CaSiO_3$ on $SiO_2$ may be prepared by a first impregnation of $CaSiO_3$ onto the $SiO_2$, followed by the co-impregnation with $Pt(NH_3)_4(NO_4)_2$ and $Bi(NO_3)_3 \cdot 5H_2O$. Again, each impregnation step may be followed by drying and calcination steps. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to use nitrogenous amine and/or nitrate based precursors.

Use of Catalyst to Hydrogenate Acetic Acid

One advantage of catalyst of the present invention is the stability or activity of the catalyst for producing an ethanol mixture. The ethanol mixture may comprise ethanol and ethyl acetate. In some embodiments, the ethanol mixture may also comprise acetaldehyde and/or acetone. In one embodiment, there may be from 5 to 95 wt. % ethanol and form 5 to 95 wt. % ethyl acetate in the ethanol mixture. Accordingly, it can be appreciated that the catalyst of the present invention is fully capable of being used in commercial scale industrial applications for hydrogenation of acetic acid, particularly in the production of ethanol and ethyl acetate. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol and ethyl acetate may be integrated with such processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g. lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of conFIGurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalyst may be used in conjunction with an inert material to regulate the pressure drop of the reactant stream through the catalyst bed and the contact time of the reactant compounds with the catalyst particles.

The hydrogenation in the reactor may be carried out in either liquid phase or vapor phase. Preferably, the reaction is carried out in the vapor phase under the following conditions. The reaction temperature will be greater than about 290° C., and may range from greater than about 290° C. to 350° C., e.g., from greater than about 290° C. to 325° C. The pressure may range from 10 kPa to 3000 kPa, e.g., from 50 kPa to 2300 kPa, from 100 kPa to 1500 kPa or from 200 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 500 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol and ethyl acetate in the reactor. For purposes of the present invention, the term "conversion" refers to the amount of acetic acid in the feed that is converted to a compound other than acetic acid. Conversion is expressed as a mole percentage based on acetic acid in the feed. The conversion may be at least 30%, e.g., at least 40%, or at least 60%. Although catalysts that have high conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. In one embodiment, catalyst selectivity to ethyl acetate and ethanol is at least 30%, e.g., at least 40%, or at least 45%. Preferred embodiments of the hydrogenation process also have low selectivity to undesirable products, such as methane, ethane, and carbon dioxide.

The term "productivity," as used herein, refers to the grams of a specified product, e.g., ethanol or ethyl acetate, formed during the hydrogenation based on the kilograms of catalyst used per hour. In terms of ethanol, for example, a productivity of at least 100 grams of ethanol/ethyl acetate per kilogram of catalyst per hour, e.g., at least 400 grams of ethanol/ethyl acetate per kilogram of catalyst per hour or at least 600 grams of ethanol/ethyl acetate per kilogram of catalyst per hour, is preferred. In terms of ranges, the productivity preferably is from 100 to 3,000 grams of ethanol/ethyl acetate per kilogram of catalyst per hour, e.g., from 400 to 2,500 grams of ethanol/ethyl acetate per kilogram of catalyst per hour or from 600 to 2,000 grams of ethanol/ethyl acetate per kilogram of catalyst per hour. Ethanol and ethyl acetate may be recovered from the product produced by the present process using several suitable separation techniques. The ethanol mixture may be used as a solvent or a feed to a hydrogenolysis reactor. In some embodiments, ethanol may be recovered from the ethanol mixture.

The ethanol separated from the ethanol mixture of the process may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The ethanol and ethyl acetate produced by the embodiments of the present invention may be used in a variety of applications including fuels, solvents, chemical feedstocks, pharmaceutical products, cleansers, sanitizers, hydrogenation transport or consumption. In fuel applications, the ethanol may be blended with gasoline for motor vehicles such as automobiles, boats and small piston engine aircraft. In non-fuel applications, the ethanol may be used as a solvent for toiletry and cosmetic preparations, detergents, disinfectants, coatings, inks, and pharmaceuticals. The ethanol and ethyl acetate may also be used as a processing solvent in manufacturing processes for medicinal products, food preparations, dyes, photochemicals and latex processing.

The ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the ethanol may be esterified with acetic acid. In another application, the ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalyst and process of this invention.

EXAMPLES

Catalysts

The catalyst supports for the examples are dried at 120° C. overnight under circulating air prior to use. All $SiO_2$ support materials are used as a 14/30 mesh or in original shape (1/16 inch or 1/8 inch pellets) unless mentioned otherwise.

First, an aqueous suspension of colloidal $SiO_2$ (15 wt. % solution, NALCO) is prepared. The suspension is stirred for 2 hours at room temperature and then added to 10.0 g of $SiO_2$ support (14/30 mesh) using incipient wetness technique. After standing for 2 hours, the material is evaporated to dryness, followed by drying at 120° C. overnight under circulating air and calcination at 500° C. for 6 hours.

Active metals are added to individual samples of the support as follows: $Pt(NH_3)_4(NO_3)_2$ (from Aldrich) and $Bi(NO_3)_3 \cdot 5H_2O$ (from Alfa Aesar) are added to form the Pt/Bi-containing Catalysts A and B. In each instance, the metal compound is placed in a vile containing diluted glacial acetic acid (from Fisher), stirred at room temperature for 15 minutes, and then added drop wise to the support material in a 100 ml round-bottomed flask. The metal solution is stirred continuously until all of the metal mixture has been added to the support while rotating the flask after every addition of metal solution. After completing the addition of the metal solution, the flask containing the impregnated catalyst is left standing at room temperature for two hours. The flask is then attached to a rotor evaporator (bath temperature at 80° C.), and evacuated until dried while slowly rotating the flask. The material is then dried further overnight at 120° C., and then calcined using the following temperature program: 25→160° C./ramp 5.0 deg/min; hold for 2.0 hours; 160→500° C./ramp 2.0 deg/min; hold for 4 hours. Each of the Catalysts A and B comprises an excess molar amount of the respective Group VIII metal, i.e. platinum.

As comparatives, catalysts not having an excess molar amount of Group VIII metal were also prepared in the same metal loading as Catalyst A and B. Table 1 summarizes the catalysts prepared.

TABLE 1

| Catalyst | Support Modifier | Metal Content (wt. %) | First Active Metal | Second Active Metal |
|---|---|---|---|---|
| A | $SiO_2$ | 0.75 | Pt (75 mol. %) | Bi |
| B | $SiO_2$ | 1.25 | Pt (75 mol. %) | Bi |
| C | SiO2 | 0.75 | Pt (50 mol. %) | Bi |
| D | SiO2 | 1.25 | Pt (50 mol. %) | Bi |
| E | SiO2 | 0.75 | Pt (25 mol. %) | Bi |
| F | SiO2 | 1.25 | Pt (25 mol. %) | Bi |

Conversion Examples

Catalysts A through F are placed in separate reactor vessels and dried by heating at 120° C. Feedstock acetic acid vapor is then charged to the reactor vessels along with hydrogen and helium as a carrier gas with an average combined gas hourly space velocity of 2430 hr$^{-1}$, temperature of 300° C., pressure of 2500 kPa, and mole ratio of hydrogen to acetic acid of 8:1. Product samples are taken and analyzed at 60 and 80 hours of reaction time to determine conversion of acetic acid. Analysis of the products is carried out by online GC. A three channel compact GC equipped with one flame ionization detector (FID) and 2 thermal conducting detectors (TCD) is used to analyze the feedstock reactant and reaction products. The front channel is equipped with an FID and a CP-Sil 5 (20 m)+WaxFFap (5 m) column and is used to quantify: acetaldehyde; ethanol; acetone; methyl acetate; vinyl acetate; ethyl acetate; acetic acid; ethylene glycol diacetate; ethylene glycol; ethylidene diacetate; and paraldehyde. The middle channel is equipped with a TCD and Porabond Q column and is used to quantify: $CO_2$; ethylene; and ethane. The back channel is equipped with a TCD and Porabond Q column and is used to quantify: helium; hydrogen; nitrogen; methane; and carbon monoxide.

Table 2 summarizes the results of the conversion examples. Conversion of acetic acid is reported at 60 and 80 hours time on stream (TOS).

TABLE 2

| | Conversion of Acetic Acid (%) | |
|---|---|---|
| Catalyst | 60 hours | 80 hours |
| A | 18% | 20% |
| B | 18% | 19% |
| C | 8% | 7% |
| D | 10% | 9.5% |
| E | 11.5% | 10% |
| F | 15% | 13% |

Catalyst A and B demonstrated improved conversion and stability over comparative Catalysts C-F. In addition, Catalyst B produced an ethanol mixture comprising 5 wt. % ethanol, and ethyl acetate 39 wt. %.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A catalyst composition comprising from 0.25 wt. % to 1.5 wt. % active metals on a support selected from the group consisting of silica, alumina, titania, silica/alumina, calcium metasilicate, pyrogenic silica, high purity silica, zirconia, carbon, zeolite and mixtures thereof, wherein the active metals comprise at least one Group VIII metal and bismuth, and wherein the catalyst composition comprises an excess molar amount of the at least one Group VIII metal.

2. The catalyst composition of claim 1, wherein the support material is selected from the group consisting of silica, alumina, silica/alumina, calcium metasilicate, and mixtures thereof.

3. The catalyst composition of claim 1, wherein the support material is present in an amount from 25 wt. % to 99 wt. %, based on the total weight of the catalyst.

4. The catalyst composition of claim 1, wherein the support further comprises a support modifier.

5. The catalyst composition of claim 4, wherein the support modifier is present in an amount from 0.1 wt. % to 50 wt. %, based on the total weight of the catalyst.

6. The catalyst composition of claim 4, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

7. The catalyst composition of claim 4, wherein the support modifier is calcium metasilicate.

8. The catalyst composition of claim 4, wherein the support modifier is selected from the group consisting of $TiO_2$, $ZrO_2$, $Nb_2O_5$, $Ta_2O_5$, $AbO_3$, $B_2O_3$, $P_2O_5$, $Sb_2O_3$, $WO_3$, $Mo O_3$, $Fe_2O_3$, $Cr_2O_3$, $V_2O_5$, $MnO_2$, $CuO$, $Co_2O_3$, $BiO_3$ and combinations thereof.

9. The catalyst composition of claim 1, wherein the at least one Group VIII metal is selected from the group consisting of iron, cobalt, nickel, ruthenium, rhodium, platinum, palladium, and combinations thereof.

10. A catalyst composition comprising from 0.25 wt. % to 2 wt. % active metals on a support comprising a support modifier, wherein the active metals comprise at least one Group VIII metal and bismuth, wherein the catalyst composition comprises an excess molar amount of the at least one Group VIII metal, and wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

11. The catalyst composition of claim 10, wherein the support material is selected from the group consisting of silica, alumina, titania, silica/alumina, calcium metasilicate, pyrogenic silica, high purity silica, zirconia, carbon, zeolite and mixtures thereof.

12. The catalyst composition of claim 10, wherein the support modifier is present in an amount from 0.1 wt. % to 50 wt. %, based on the total weight of the catalyst.

13. The catalyst composition of claim 10, wherein the at least one Group VIII metal is selected from the group consisting of iron, cobalt, nickel, ruthenium, rhodium, platinum, palladium, and combinations thereof.

14. The catalyst composition of claim 10, wherein the support material comprises silica having a surface area of from 50 to 600 $m^2/g$.

15. The catalyst composition of claim 10, wherein the support material comprises silica having a surface area of at least about 250 $m^2/g$.

16. A process for producing ethanol and ethyl acetate comprising contacting a feedstock comprising acetic acid and hydrogen in a reaction zone at hydrogenation conditions including a temperature of greater than about 290° C. with a catalyst composition, wherein the catalyst composition comprises from 0.25 wt. % to 2 wt. % active metals on a support selected from the group consisting of silica, alumina, titania, silica/alumina, calcium metasilicate, pyrogenic silica, high purity silica, zirconia, carbon, zeolite and mixtures thereof, wherein the active metals comprise at least one Group VIII metal and bismuth, and where the catalyst composition comprises an excess molar amount of the at least one Group VIII metal.

17. The process of claim 16, wherein acetic acid conversion is greater than 30%.

18. The process of claim 16, wherein the hydrogenation conditions include a temperature of from greater than about 290° C. to 350° C., a pressure of 10 kPa to 3000 kPa, and a hydrogen to acetic acid mole ratio of greater than 4:1.

19. The process of claim 16, which further comprises gasifying a carbonaceous material to produce components of the feedstock.

20. The process of claim 19, wherein the carbonaceous material is selected from the group consisting of oil, coal, natural gas and biomass.

* * * * *